US008644521B2

(12) United States Patent
Christoph et al.

(10) Patent No.: US 8,644,521 B2
(45) Date of Patent: Feb. 4, 2014

(54) ADAPTIVE NOISE CONTROL SYSTEM WITH SECONDARY PATH ESTIMATION

(75) Inventors: Markus Christoph, Straubing (DE); Michael Wurm, Straubing (DE)

(73) Assignee: Harman Becker Automotive Systems GmbH, Karlsbad (DE)

( * ) Notice: Subject to any disclaimer, the term of this patent is extended or adjusted under 35 U.S.C. 154(b) by 1012 days.

(21) Appl. No.: 12/696,862

(22) Filed: Jan. 29, 2010

(65) Prior Publication Data

US 2010/0195844 A1 Aug. 5, 2010

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04B 15/00*** | (2006.01) |

(52) U.S. Cl.
USPC ..... 381/71.1; 381/71.2; 381/71.9; 381/71.11; 381/94.7

(58) Field of Classification Search
USPC ......... 381/71.1, 71.2, 71.11, 71.8, 71.9, 94.1, 381/94.7, 94.9
See application file for complete search history.

(56) References Cited

U.S. PATENT DOCUMENTS

| | | | |
|---|---|---|---|
| 5,384,853 A | 1/1995 | Kinoshita et al. | |
| 2005/0207585 A1 | 9/2005 | Christoph | |
| 2008/0181422 A1 | 7/2008 | Christoph | |
| 2009/0086990 A1 * | 4/2009 | Christoph | 381/71.12 |

FOREIGN PATENT DOCUMENTS

| | | |
|---|---|---|
| JP | 09195791 | 7/1997 |
| JP | 2003202870 | 7/2003 |
| JP | 2008015046 | 1/2008 |

OTHER PUBLICATIONS

Kou et al., "Active Noise Control: A Tutorial Review," Proceedings of the IEEE, IEEE. New York, US, vol. 87, No. 6, Jun. 1, 1999, pp. 943-973.
Eriksson et al., "use of Random Noise for On-line Transducer Modeling in an Adaptive Active Attenuation System," Journal of the Acoustical Society of America, AIP/Acoustical Society of America, Melville, NY, US, vol. 85, No. 2, Feb. 1, 1989, pp. 797-802.

* cited by examiner

*Primary Examiner* — Vivian Chin
*Assistant Examiner* — Douglas Suthers
(74) *Attorney, Agent, or Firm* — O'Shea Getz P.C.

(57) ABSTRACT

An active noise cancellation system includes an adaptive filter, a signal source, an acoustic actuator, a microphone, a secondary path and an estimation unit. The adaptive filter receives a reference signal representing noise, and provides a compensation signal in response to the received reference signal. The signal source provides a measurement signal. The acoustic actuator radiates the compensation signal and the measurement signal to the listening position. The microphone receives a first signal that is a superposition of the radiated compensation signal, the radiated measurement signal, and the noise signal at the listening position, and provides a microphone signal in response to the received first signal. The secondary path includes a secondary path system that represents a signal transmission path between an output of the adaptive filter and an output of the microphone. The estimation unit estimates a transfer characteristic of the secondary path system in response to the measurement signal and the microphone signal.

20 Claims, 8 Drawing Sheets

ADAPTIVE NOISE CONTROL SYSTEM WITH SECONDARY PATH ESTIMATION

1. CLAIM OF PRIORITY

This patent application claims priority from European Patent Application No. 09 151 815.9 filed on Jan. 30, 2009, which is hereby incorporated by reference in its entirety.

2. FIELD OF TECHNOLOGY

The present invention relates to an active noise control system and, more particularly, to system identification in active noise control systems.

3. RELATED ART

Noise (or "disturbing sound"), in contrast to a useful sound signal, is a sound that is not intended to be perceived by a receiver (e.g., a listener). For example, as related to a motor vehicle, noise can include sound signals generated by mechanical vibrations of an engine, fans or vehicle components mechanically coupled to the engine or fans, and sound generated by the tires and the wind. Typically, generation of noise may be divided into three sub-processes: (i) generation of the noise by a noise source, (ii) transmission of the noise away from the noise source, and (iii) radiation of the noise signal.

Noise within a listening room can be suppressed using a variety of techniques. For example, noise may be reduced or suppressed by damping the noise signal at the noise source. The noise may also be suppressed by inhibiting or damping transmission and/or radiation of the noise. In many applications, however, these noise suppression techniques do not reduce noise levels in the listening room below an acceptable limit. This is especially true for noise signals in the bass frequency range. Noise may also be suppressed using destructive interference, i.e. by superposing the noise signal with a compensation signal. Typically, such noise suppression systems are referred to as "active noise cancelling" or "active noise control" (ANC) systems.

Although it is known that "points of silence" may be achieved in a listening room using destructive interference, where the compensation sound signal is superposed with the noise signal. A practical technical implementation of this technique, however, has not been feasible to date due to a lack of cost effective high performance digital signal processors for use with sensors and actuators.

Modern active noise reduction or suppression systems (i.e., "active noise control" or "ANC" systems) typically generate a compensation sound signal that is superposed with a noise signal. The compensation signal has amplitude and frequency components that are equal to those of the noise signal; however, it is phase shifted by 180°. As a result, the compensation sound signal destructively interferes with the noise signal, thereby eliminating or damping the noise signal at least at certain positions within the listening room.

Many modern motor vehicles include a so-called "rear seat entertainment" system that provides high-fidelity audio presentation using a plurality of loudspeakers arranged within the vehicle passenger compartment. In order to improve sound reproduction of such a rear seat entertainment system, an active noise control system can suppress disturbing noise signals during digital audio processing. In addition, the active noise control system may facilitate conversations between people sitting on the rear seats and people sitting on the front seats.

Typically, active noise control systems use digital signal processing and digital filtering techniques. For example, a noise sensor such as, for example, a microphone or a non-acoustic sensor may be used to obtain an electrical reference signal representing the disturbing noise signal generated by a noise source. This reference signal is fed to an adaptive filter. The filtered reference signal is then supplied to an acoustic actuator (e.g., a loudspeaker) that generates a compensation sound field, which has an opposite phase to the noise signal, within a portion of the listening room. This compensation field thus damps or eliminates the noise signal within this portion of the listening room. A residual noise signal may be measured using a microphone. The microphone provides an "error signal" to the adaptive filter, where filter coefficients of the adaptive filter are modified such that a norm (e.g., power) of the error signal is reduced.

The adaptive filter may use known digital signal processing methods, such as an enhanced least mean squares (LMS) method, to reduce the error signal, or more specifically, the power of the error signal. Examples of such enhanced LMS method include a filtered-x-LMS (FXLMS) algorithm or modified versions thereof, or a filtered-error-LMS (FELMS) algorithm.

A model that represents an acoustic transmission path from the acoustic actuator (i.e., the loudspeaker) to the error signal sensor (i.e., the microphone) is used when applying the FXLMS (or any related) algorithm. This acoustic transmission path from the loudspeaker to the microphone is usually referred to as a "secondary path" of the ANC system. In contrast, the acoustic transmission path from the noise source to the microphone is usually referred to as a "primary path" of the ANC system.

The transmission function (i.e., the frequency response) of the secondary path system of the ANC system typically has a considerable impact on the convergence behaviour of an adaptive filter that uses the FXLMS algorithm, and thus on the stability behaviour thereof, and on the speed of the adaptation. Thus, a varying secondary path transmission function can have a substantial negative impact on the performance of the active noise control system, especially on the speed and the quality of the adaptation achieved by the FXLMS algorithm. This is due to the fact that the actual secondary path transmission function, when subjected to variations, no longer matches an "a priori" identified secondary path transmission function that is used within the FXLMS (or related) algorithms.

There is a general need to provide active noise control that can improve adaptation speed and adaptation quality, as well as robustness of the entire single-channel or multi-channel active noise control system.

SUMMARY OF THE INVENTION

An active noise cancellation system includes an adaptive filter, a signal source, an acoustic actuator, a microphone, a secondary path and an estimation unit. The adaptive filter receives a reference signal representing noise, and provides a compensation signal in response to the received reference signal. The signal source provides a measurement signal. The acoustic actuator radiates the compensation signal and the measurement signal to the listening position. The microphone receives a first signal that is a superposition of the radiated compensation signal, the radiated measurement signal, and the noise signal at the listening position, and provides a microphone signal in response to the received first signal. The secondary path includes a secondary path system that represents a signal transmission path between an output of the adaptive filter and an output of the microphone. The estimation unit estimates a transfer characteristic of the secondary path system in response to the measurement signal and the microphone signal.

BRIEF DESCRIPTION OF THE DRAWINGS

The invention can be better understood with reference to the following drawings and description. The components in the figures are not necessarily to scale, instead emphasis is placed upon illustrating the principles of the invention. Moreover, in the figures, like reference numerals designate corresponding parts. In the drawings.

DETAILED DESCRIPTION

An exemplary active noise control system (hereinafter the "ANC system") is disclosed that improves music reproduction and/or speech intelligibility, (i) in an interior (e.g., a passenger compartment) of a motor vehicle or (ii) for an active headset, by suppressing undesired noise signals. Specifically, this ANC system uses destructive interference by generating and superposing a compensation signal with a disturbing sound signals (i.e., noise), where the compensation signal has an opposite phase to that of the disturbing sound signal. In an ideal case, a complete elimination of the undesired noise signal is thereby achieved.

Figure 1:
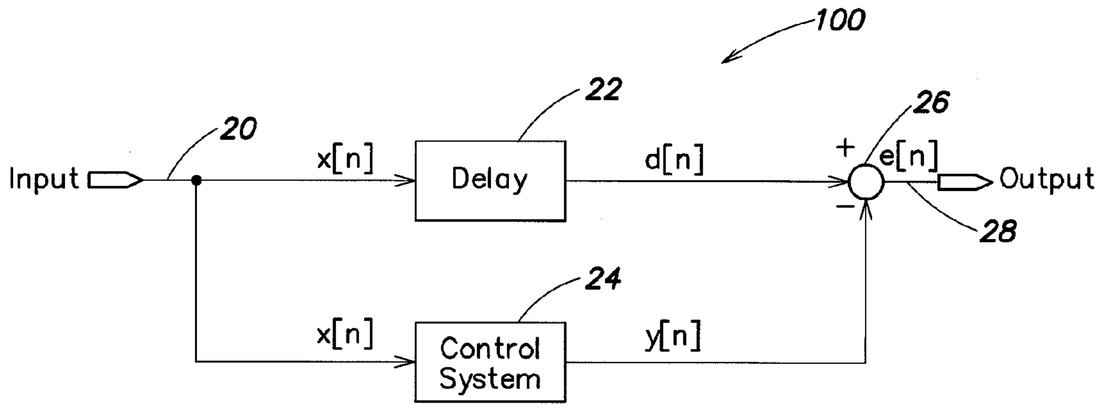
FIG. 1 illustrates of a basic feedforward system.

Referring to FIG. 1, a simplified example of a feedforward ANC system 100 uses a reference signal x[n], that is correlated with a noise signal d[n] to generate a compensation signal y[n] for supplying to a compensation actuator such as a loudspeaker (not shown). An error signal (i.e., residual noise signal) e[n] is provided when the compensation signal y[n] is subtracted from the noise signal d[n] (i.e., when the compensation signal is superposed with the noise signal, e.g., in the vehicle passenger compartment). In contrast, referring to FIG. 2, a simplified example of a feedback ANC system 200 generates a compensation signal y[n] from a system response. In practice the "system" is the overall transmission path from the noise source to a listening position where noise cancellation is desired. The "system response" to a noise input from the noise source is represented by at least one microphone output signal which is fed back via a control system to the loudspeaker generating "anti-noise" for suppressing the actual noise signal at the listening position.

Feedforward systems are typically more effective than feedback systems, in particular due to the possibility of the broadband reduction of disturbing noises. This is a result of the fact that a signal representing the disturbing noise (i.e., the reference signal x[n]) may be directly processed and used for actively counteracting the disturbing noise signal d[n].

Referring again to FIG. 1, an input signal x[n] (e.g. the noise signal at the noise source or a signal derived therefrom and correlated thereto) is supplied via line 20 to a primary path system 22 and a control system 24. The primary path system 22 delays the input signal x[n] for a period that corresponds to, for example, a propagation time as the noise travels from the noise source to that portion of the listening room (i.e., the listening position) where a suppression of the disturbing noise signal is to be achieved (i.e., to the desired "point of silence"). The control system 24 filters the reference signal x[n] such that the filtered reference signal y[n], when superposed with the noise signal d[n] by the summer 26, compensates for the noise due to destructive interference at the listening position. The summer 26 outputs an error signal e[n] on line 28. The error signal e[n] is a residual signal that includes the signal components of the disturbing noise signal d[n] that were not suppressed by the superposition with the filtered reference signal y[n]. The signal power of the error signal e[n] may be regarded as a quality measure for the noise cancellation achieved.

Figure 2:
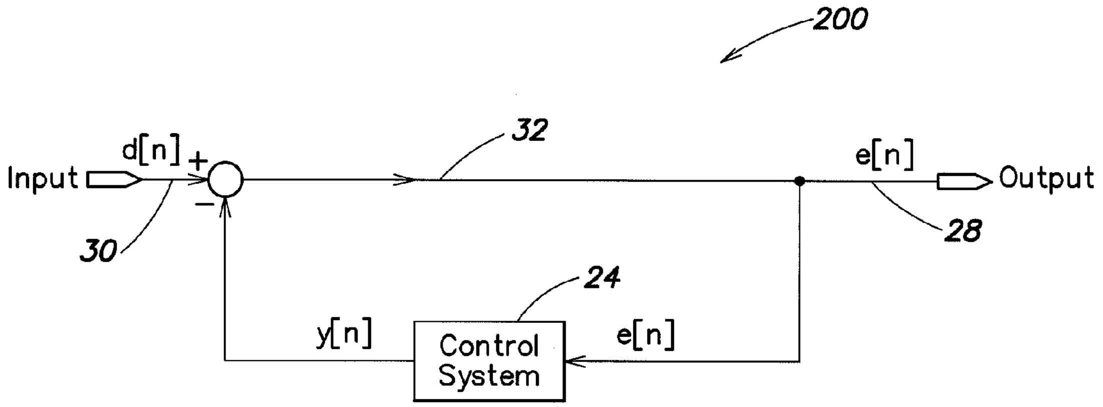
FIG. 2 illustrates of a basic feedback system.

Referring to FIG. 2, effects of a noise disturbance in the feedback system 200 are initially unknown. Thus, noise suppression (active noise control) in the system begins when a sensor (not shown) determines the effects of the noise disturbance. This enables the feedback system, in contrast to feedforward systems, to operate even where a suitable signal (i.e., the reference signal x[n]) correlated to the disturbing noise d[n] is unavailable. This is particularly advantageous, for example, when using ANC systems in unknown environments and where specific information about the noise source is unavailable.

An input signal (i.e., the noise signal d[n]), on line 30, is suppressed by a filtered input signal (i.e., the compensation signal y[n]) provided by the feedback control system 24. The residual signal (i.e., the error signal e[n]) on line 32 serves as an input for the feedback loop 24.

In preferred embodiments, noise suppression systems are adaptive because the noise level and the spectral composition of the noise, which is to be reduced, may be, for example, subject to chronological changes due to changing ambient conditions. For example, when ANC systems are used in motor vehicles, ambient conditions may frequently change due to, for example, different driving speeds (wind noises, tire rolling noises), different load states and engine speeds or by one or more open windows. Moreover the transfer functions of the primary and the secondary path systems may change over time.

An unknown system may be iteratively estimated using an adaptive filter. Filter coefficients for the adaptive filter are modified such that the transfer characteristic of the adaptive filter approximately matches the transfer characteristic of the unknown system. In ANC applications, the adaptive filters may be configured as digital filters such as, but not limited to, finite impulse response (FIR) or infinite impulse response (IIR) filters whose filter coefficients are modified according to a given adaptation algorithm.

The adaptation of the filter coefficients is a recursive process which, for example, optimizes the filter characteristic of the adaptive filter by reducing the error signal (i.e., the difference between the output of the unknown system and the adaptive filter, wherein both are supplied with the same input signal). When the norm (i.e., the power) of the error signal approaches zero, the transfer characteristic of the adaptive filter approaches the transfer characteristic of the unknown system. The unknown system may thereby represent the path (i.e., the primary path) of the noise signal from the noise source to the listening position. The noise signal is thereby "filtered" by the transfer characteristic of the signal path which, in the case of a motor vehicle, includes the passenger compartment (primary path transfer function). The primary path may also include the transmission path from the actual noise source (e.g., the engine, the tires) to the car-body and further to the passenger compartment as well as the transfer characteristics of the microphones used.

Figure 3:
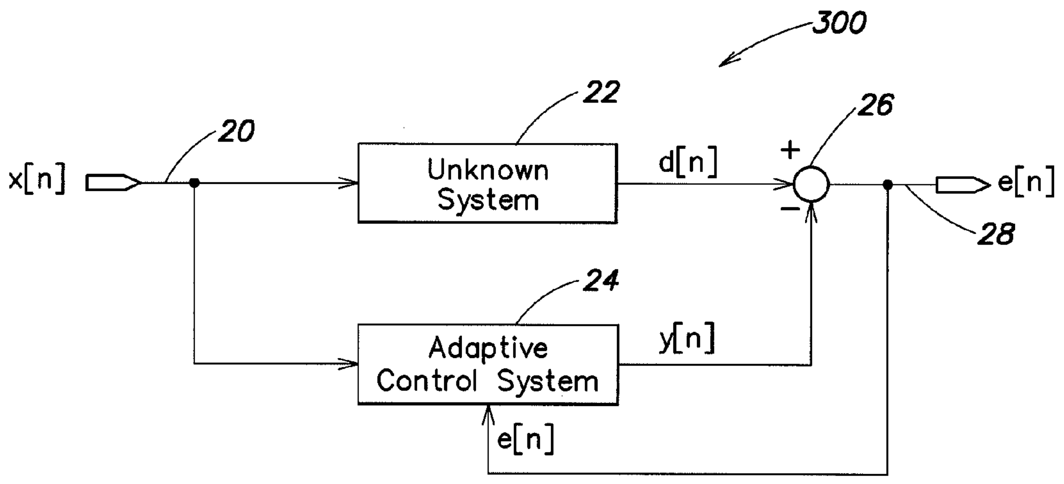
FIG. 3 illustrates a system that includes an adaptive filter.

FIG. 3 illustrates a system 300 for estimating an unknown system 22 using an adaptive filter 24. The input signal x[n] is supplied on the line 20 to the unknown system 22 and to the adaptive filter 24. The output signal d[n] of the unknown system 22 and the output signal y[n] of the adaptive filter 24 are destructively superposed (i.e., subtracted) by a difference unit 26. The difference unit 26 outputs a residual signal (i.e., the error signal e[n]) on line 28 to the adaptive filter 24, which implements an adaptation algorithm. The adaptation algorithm, such as a least mean square (LMS) algorithm, calculates modified filter coefficients such that the norm (i.e., the power) of the error signal e[n] is reduced. In this case, the output signal d[n] of the unknown system 22 is suppressed and the transfer characteristics of the adaptive control system 24 match the transfer characteristic of the unknown system 22.

The LMS algorithm is used to approximate a solution for the least mean squares problem. This algorithm may be implemented, for example, using digital signal processors. The LMS algorithm is based on a method of the steepest descent (or "gradient descent method"), and computes a gradient in a simple manner. The algorithm thereby operates in a time-recursive fashion. That is, the algorithm is re-run for each new data set, thereby updating the solution. Due to its relative simplicity in small memory requirements, the LMS algorithm is often used for adaptive filters and for adaptive control. In other embodiments, the LMS may be based on other methods such as recursive least squares, QR decomposition least squares, least squares lattice, QR decomposition lattice or gradient adaptive lattice, zero-forcing, stochastic gradient, etc.

Figure 4:
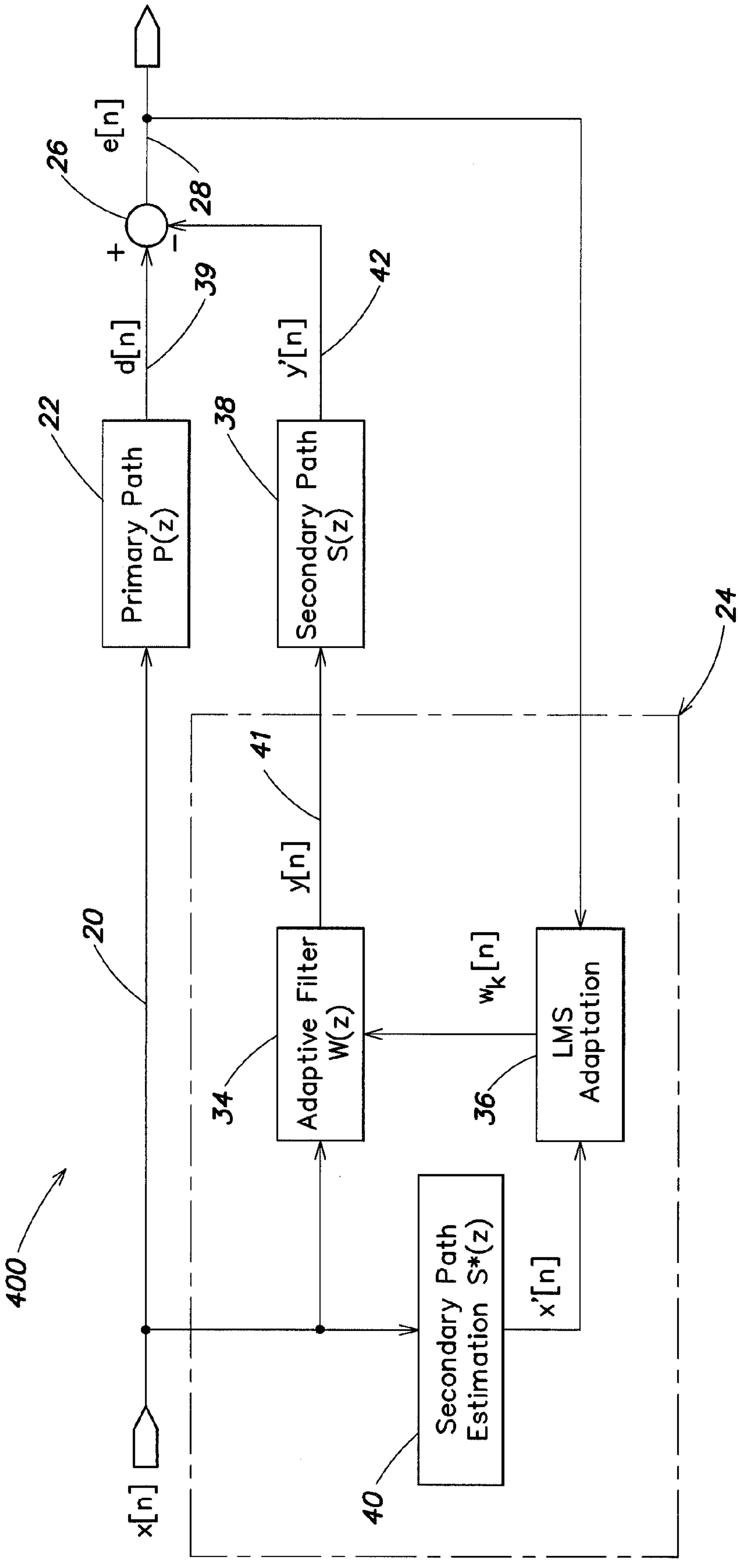
FIG. 4 illustrates a single-channel active noise control system using a filtered-x-LMS (FXLMS) processor.

The ANC system may use the filtered-x-LMS (FXLMS) algorithm, or modifications or extensions thereof such as the modified filtered-x LMS (MFXLMS) algorithm. FIG. 4 illustrates an embodiment of a digital feedforward ANC system 400 that uses the FXLMS algorithm. Components, such as, for example, amplifiers, analog-to-digital converters and digital-to-analog converters, which are included in an actual realization of the ANC system, are not illustrated herein to simplify the following description. All signals are denoted as digital signals with the time index n placed in squared brackets.

The ANC system 400 includes the primary path system 22 having a (discrete time) transfer function P(z) representing the transfer characteristics of the signal path between the noise source and the listening position (i.e., where the noise is to be suppressed). The ANC system 400 also includes an adaptive filter 34 having a filter transfer function W(z), and an adaptation unit 36 for calculating a set of filter coefficients $w_k=(w_0, w_1, w_2, \ldots)$ for the adaptive filter 34. A secondary path system 38 having a transfer function S(z) is configured downstream of the adaptive filter 34 and represents the signal path between a loudspeaker (not shown) that radiates the compensation signal y'[n] and the listening position. The secondary path 38 includes the transfer characteristics of all components downstream of the adaptive filter 34; e.g., amplifiers, digital-to-analog-converters, loudspeakers, acoustic transmission paths, microphones, and analog-to-digital-converters. An estimation S*(z) 40 of the secondary path transfer function S(z) is used to calculate the filter coefficients. The primary path system 22 and the secondary path system 38 are "real" systems essentially representing the physical properties of the listening room, wherein the other transfer functions are implemented in a digital signal processor.

The input signal x[n] is transported to a listening position via the primary path system 22 which provides the disturbing noise signal d[n] on line 39. The reference signal x[n] is also supplied to the adaptive filter 34, which imposes a 180 degree phase shift thereto to output a filtered signal y[n] on line 41. The filtered signal y[n] is supplied to the secondary path system 38, which provides a modified filtered signal y'[n] (i.e., the compensation signal) on line 42. The modified filtered signal y'[n] on line 42 and the noise signal d[n] on line 39 are destructively superposed in the system 26. The system 26 outputs a measurable residual signal on the line 28 that is used as an error signal e[n] for the adaptation unit 36. An estimated model S*(z) of the secondary path transfer function S(z) is used to calculate updated filter coefficients $w_k$. This compensates for decorrelation between the filtered reference signal y[n] and the compensation signal y'[n] due to signal distortion in the secondary path 38. The secondary path estimation system 40 also receives the input signal x[n] on the line 20 and provides a modified reference signal x'[n] to the adaptation unit 36.

The overall transfer function W(z)·S(z) of the series connection of the adaptive filter 34 and the secondary path system 38 approaches the primary path transfer function P(z) (see the primary path system 22). The adaptive filter 34 phase shifts the input signal x[n] by 180° such that the disturbing noise signal d[n] (output of the primary path 22) and the compensation signal y'[n] (output of the secondary path 38) are destructively superposed, thereby suppressing the noise signal d[n] at the listening position.

The residual error signal e[n], which may be measured by a microphone, and the modified input signal x'[n], which are provided by the secondary path estimation system 40, are supplied to the adaptation unit 36. The adaption unit 36 calculates the filter coefficients $w_k$ for the adaptive filter 34 from the modified reference signal x'[n] ("filtered x") and the error signal e[n] such that the norm (i.e., the power or $L_2$-Norm) of the error signal ||e[n]|| is reduced. These filter coefficients may be calculated using the LMS algorithm, as set forth above. The circuit blocks 34, 36, and 40 are included in the ANC unit 24, which may be implemented in a digital signal processor. Of course alternatives or modifications of the "filtered-x LMS" algorithm, such as, for example, the "filtered-e LMS" algorithm, are also applicable.

In some cases, the adaptivity of the algorithms for the digital ANC system, such as the FXLMS algorithm, may cause instabilities. Disadvantageously, such instabilities may, for example, cause self-oscillations and similar undesirable effects in the ANC systems, which may be perceived as unpleasant noise such as whistling, screeching, et cetera.

In adaptive ANC systems that use LMS-type algorithms to adapt the filter characteristics, instabilities can occur, for example, when the reference signal x[n] of the ANC arrangement rapidly changes over time, and thus includes, e.g., transient, impulse-containing sound components. Such instability may be a result when, e.g., a convergence parameter or step size of the adaptive LMS algorithm is not chosen properly for an adaptation to impulse-containing sounds.

The quality of the estimation (i.e., the transmission function S*(z)) of the secondary path transfer function S(z) for the secondary path system 38 may also influence the stability of the active noise control arrangement, as illustrated in FIG. 4. Deviation of the estimation S*(z) of the secondary path from the actually present transmission function S(z) of the secondary path, with respect to magnitude and phase, thereby plays an important role in convergence and the stability behavior of the FXLMS algorithm, and thus in the speed of the adaptation and the overall system performance. In this context, this is oftentimes also referred to as a "90° criterion". Deviations in the phase between the estimation of the secondary path transmission function S*(z) and the actually present transmission function S(z) of the secondary path of greater than +/−90° thereby lead to an instability of the adaptive active noise control arrangement. In addition, changes in the ambient conditions (e.g., in the passenger compartment of a vehicle), in which the active noise control arrangement is used, may also lead to instabilities. For example, the opening of a window in the driving vehicle may considerably change the acoustic environment and, therefore, also the transmission function of the secondary path of the active noise control arrangement. In some cases, the transmission function of the secondary path may change so much as to cause instability in the entire ANC system.

In practical applications, the transmission function S(z) of the secondary path may no longer be approximated with a sufficiently high quality using the a priori determined estimation S*(z). A dynamic system identification of the secondary path, which adapts itself to the changing ambient conditions in real time, may represent a solution for the problem caused by dynamic changes of the transmission function of the secondary path S(z) during operation of the ANC system.

Such a dynamic system identification of the secondary path system may be realized using an additional adaptive filter arrangement, which is connected in parallel to the secondary path system that is to be approached thereby applying the principle illustrated in FIG. 3. Optionally, a suitable measuring signal, that is independent from and uncorrelated to the reference signal x[n] of the ANC system, may be provided to the secondary path for improving dynamic and adaptive system identification of the sought secondary path transmission function S*(z). The measuring signal for the dynamic system identification can therefore be, for example, a noise-like signal or music. One example of such an ANC system with dynamic secondary path approximation is described below with reference to FIG. 7.

Figure 5:
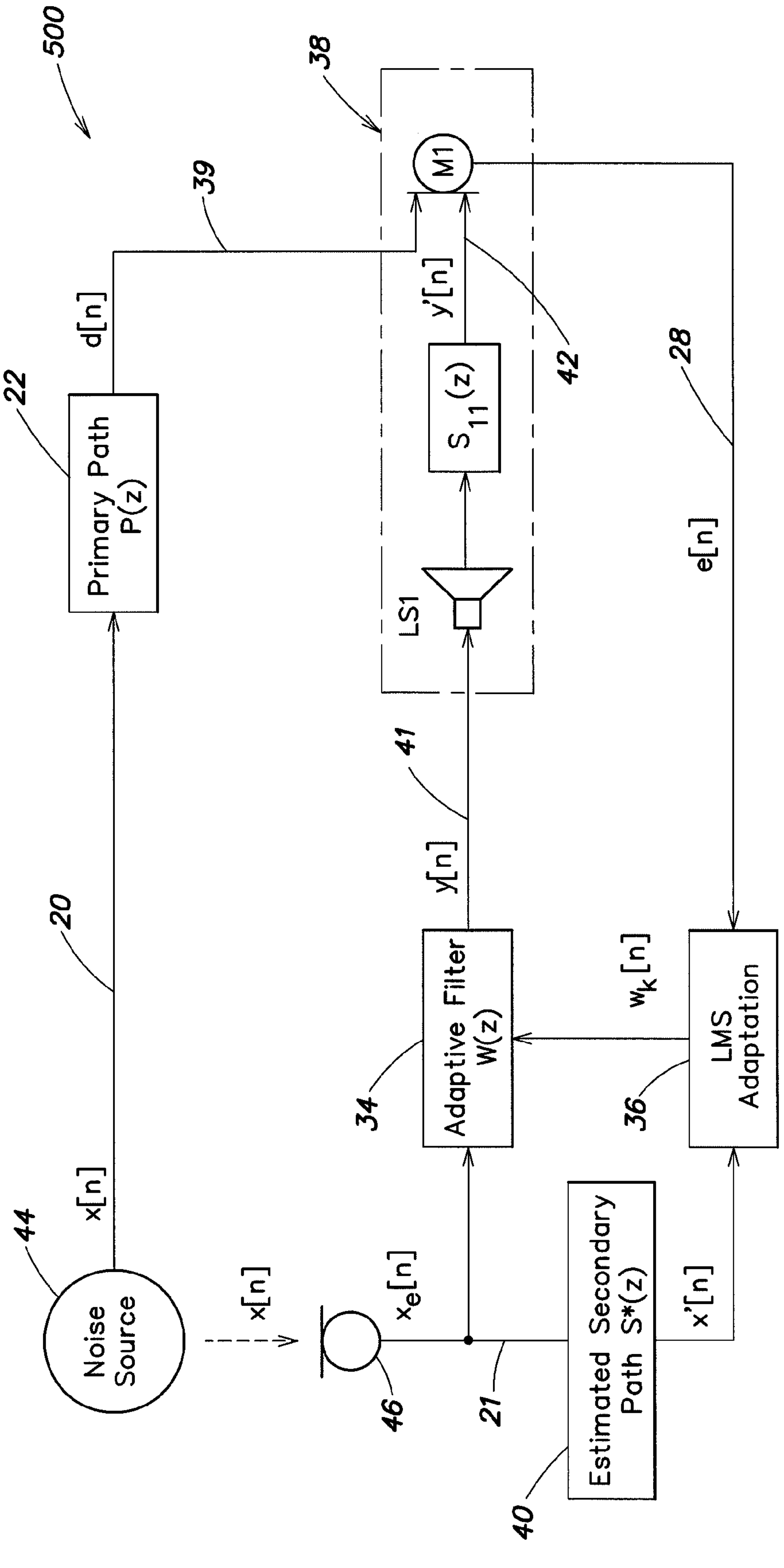
FIG. 5 illustrates, in greater detail, the single-channel ANC system in FIG. 4.

FIG. 5 illustrates an ANC system 500, similar to the system 400 in FIG. 4. The ANC system 500 is shown in a single-channel configuration to simplify the following description; however, it is not limited thereto. In contrast to the system in FIG. 4, the ANC system 500 further includes a noise source 44, a loudspeaker LS1, and a microphone M1. The noise source 44 generates the input noise signal (i.e., the reference signal x[n]). The loudspeaker LS1 radiates the filtered reference signal y[n]. The microphone M1 senses and provides a signal indicative of the residual error signal e[n]. The noise signal generated by the noise source 44 is provided to the primary path system 22. The primary path system 22 outputs the noise signal d[n] on the line 39. An electrical representation $x_e[n]$ of the input signal x[n] (i.e., the reference signal) may be provided by an acoustical sensor 46 such as a microphone or a vibration sensor that is sensitive in the audible frequency spectrum or at least in a desired spectral range thereof. The electrical representation $x_e[n]$ of the input signal x[n] (i.e., the sensor signal) is supplied to the adaptive filter 34 via line 21. The adaptive filter 34 supplies the filtered signal y[n] to the secondary path system 38 via line 41. The residual signal e[n] is measured by the microphone M1, which has an output signal that is supplied to the adaptation unit 36 as the error signal e[n] via line 28. The adaptation unit 36 calculates optimal filter coefficients $w_k[n]$, for example using the FXLMS algorithm, for the adaptive filter 34. Since the acoustical sensor 46 can detect the noise signal generated by the noise source 44 in a broad frequency band of the audible spectrum, the arrangement of FIG. 5 may be used for broadband ANC applications.

In narrowband ANC applications, the acoustical sensor 46 may be replaced by a non-acoustical sensor (e.g., a rotational speed sensor) and a signal generator for synthesizing the electrical representation $x_e[n]$ of the reference signal x[n]. The signal generator may use the base frequency, which is measured with the non-acoustical sensor, and higher order harmonics for synthesizing the reference signal $x_e[n]$. The non-acoustical sensor may be, for example, a revolution sensor that gives information on the rotational speed of the car engine which may be regarded as main noise source.

The overall secondary path transfer function S(z) includes the transfer characteristics of the loudspeaker LS1, the acoustical transmission path 38 characterized by the transfer function $S_{11}(z)$, the transfer characteristics of the microphone M1, and transfer characteristics associated with other electrical components such as amplifiers, A/D-converters and D/A-converters, etc. In this example, the single-channel ANC system 500 has one acoustic transmission path transfer function $S_{11}(z)$. In contrast, a general multi-channel ANC system, which includes a plurality of V loudspeakers LSv (v=1, . . . , V) and a plurality of W microphones Mw (w=1, . . . , W), has an overall secondary path transfer function S(z) characterized by a V×W transfer matrix of transfer functions $S_{vw}(z)$.

Figure 6:
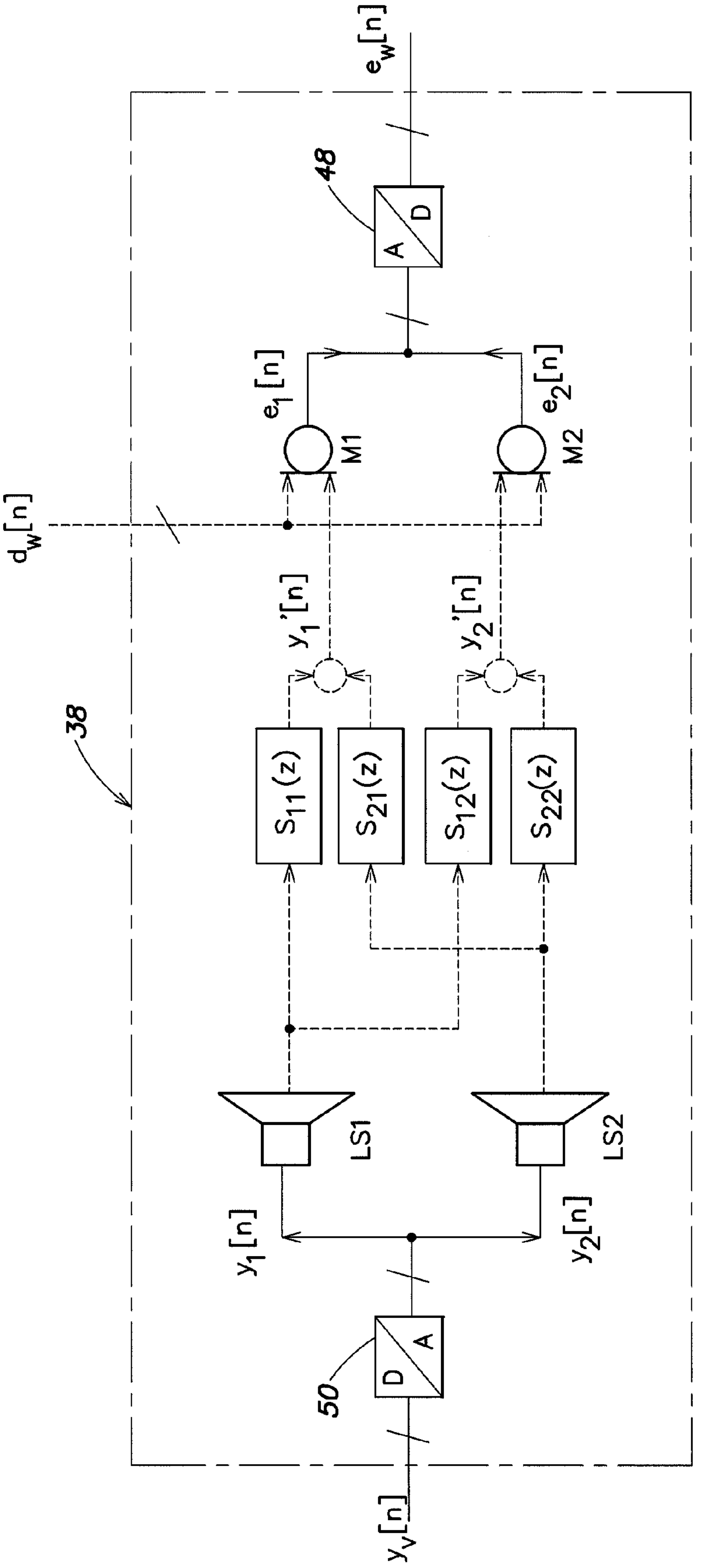
FIG. 6 illustrates a secondary path of a two-by-two multichannel ANC system.

FIG. 6 illustrates an example of an overall secondary path system 38 that includes two loudspeakers (i.e., V=2) and two microphones (i.e., W=2). In such a multi-channel ANC system, the adaptive filter 34 includes a filter $W_v(z)$ for each channel (not shown). The adaptive filters $W_v(z)$ provide a V-dimensional filtered reference signal $y_v[n]$ (v=1, . . . , V), each signal component being supplied to a respective one of the loudspeaker LSv. Each of the W microphones receives an acoustic signal from each of the V loudspeakers, resulting in a total number of V×W acoustic transmission paths (e.g., four transmission paths). In this embodiment, the compensation signal y'[n] is a W-dimensional vector $y_w'[n]$, each component of which is superposed with a corresponding disturbing noise signal component $d_w[n]$ at the respective listening position where the microphone M1 or M2 is located. The superposition $y_w'[n]+d_w[n]$ provides the W-dimensional error signal $e_w[n]$, where the compensation signal $y_w'[n]$ is at least approximately in phase opposition to a respective one of the noise signals $d_w[n]$. Furthermore, A/D-converters 48 and D/A-converters 50 are illustrated in FIG. 6.

Figures 7A, 7B:
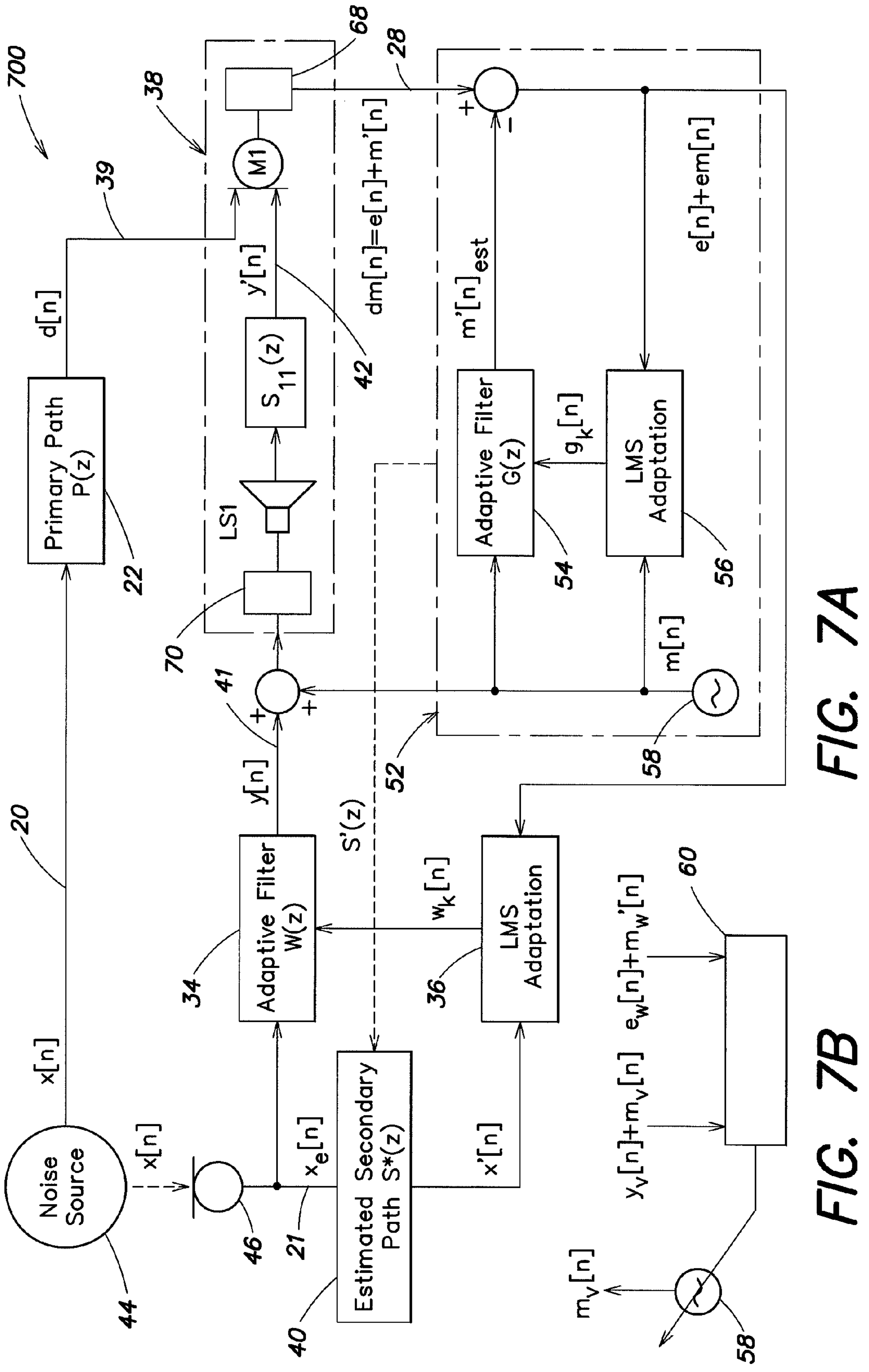
FIGS. 7A and 7B illustrate a single-channel ANC system that includes a secondary path identification system.

Referring to FIG. 7A, a single-channel ANC system 700 is configured to provide an additional dynamic estimation of the secondary path transfer function S*(z) for use with the FXLMS algorithm. The system 700 includes the components from the system in FIG. 5 in addition to an additional secondary path estimation system 52 for system estimation of the secondary path transfer function S(z). The estimated secondary path transfer function S*(z) may then be used within the FXLMS algorithm for calculating the filter coefficients of the adaptive filter 34. The secondary path estimation realizes the structure already illustrated in FIG. 3.

The additional secondary path estimation system 52 includes an adaptive filter 54, a LMS adaptation unit 56, and a measurement signal generator 58. The adaptive filter 54 has an adaptable transfer function G(z), and is connected in parallel to the transmission path of the secondary path system 38. A measurement signal m[n] is generated by the measurement signal generator 58 and superposed with the compensation signal y[n] (i.e., to the output signal of the adaptive filter 34). The output signal $m'[n]_{est}$ of the adaptive filter 54 is subtracted from the microphone signal dm[n]=e[n]+m'[n] on line 28 and the resulting residual signal $e_{tot}$[n]=e[n]+(m'[n]−m'[n]$_{est}$) is used as error signal for calculating updated filter coefficients $g_k$[n] for the adaptive filter 54. The updated filter coefficients $g_k$[n] are calculated by the LMS adaptation unit 56. In this embodiment, the transfer function G(z) of the adaptive filter 54 follows the transfer function S(z) of the secondary path 38 even where the transfer function S(z) varies over time. The transfer function G(z) may be used as an estimation S*(z) of the secondary path transfer function within the FXLMS algorithm. It is desirable that the measurement signal m[n] is uncorrelated with the reference signal x[n] and thus uncorrelated with the disturbing noise signal d[n] and the compensation signal y'[n] in order to enhance performance of the dynamic secondary path system estimation. In this case, the reference signal as well as the ANC error signal e[n] are uncorrelated noise for the secondary path system estimation 52 and therefore do not result in any systematic errors.

Furthermore, it may be desirable to dynamically adjust the level and spectral composition of the measuring signal m[n] from the measurement signal generator 58 such that the listener cannot hear it in the acoustic environment, even though it covers the respective active spectral range of the variable secondary path (system identification). This may be attained by dynamically adjusting the level and the spectral composition of the measuring signal in such a manner that this measuring signal is reliably covered or masked by other signals, such as speech or music. Additionally, where the power of the error signal e[n] (which is uncorrelated noise for the secondary path system estimation 52) increases in one or more frequency bands, the measurement signal m[n] (and thus the output signal m'[n]$_{est}$ of the adaptive filter 54 as well as the output signal of the secondary path system m'[n]) may also be subjected to a corresponding frequency dependent gain, such to increase signal-to-noise ratio SNR(m'[n], e[n]) in the corresponding frequency bands. Such a "gain shaping" of the measurement signal may significantly improve the quality of the system estimation. A good performance of the system identification is achieved where the power of that part of the output signal of the secondary path system m'[n] is higher than the ANC error signal e[n]. The amplitude of the measurement signal m[n] provided by signal generator 58 may be (frequency dependently) set dependent on a (frequency dependent) quality function QLTY which is, for example the above mentioned signal to noise ratio SNR or any function or value derived therefrom. In the case of a multi-channel ANC system, the quality function is a V×W two-dimensional matrix $QLTY_{v,w}$ representing the signal-to-noise ratio (or any derived value) of the measurement signal $m_v$[n] radiated from the $v^{th}$ loudspeaker LSv and the noise signal $e_w$[n] at the $w^{th}$ microphone Mw.

Dependent on the actual value of the quality function QLTY (or $QLTY_{vw}$ in the multi-channel case), the amplification factor of the measurement signal generator 58 may be set to provide a quality function value greater than a threshold representing a desired minimum quality of the adaptation process of adaptive filter 54. For example, where an actual value of the quality function QLTY is greater than a predefined threshold, then the quality of system identification of the secondary path is sufficient and the amplification factor may be reduced or maintained. Where the value of the quality function QLTY is smaller than the threshold, the secondary path identification is unreliable and the signal amplitude of the measurement signal m[n] should be increased by increasing the amplification of the measurement signal generator. The quality function may be evaluated and the measurement signal amplitude may be adjusted during operation of the ANC system in regular time intervals. The amplification factor of the measurement signal generator 58 (i.e., the signal gain) is adaptively adjusted in this way. This adaptation of the measurement signal gain is depicted in FIG. 7B. A quality function calculation unit 60, for example, receives the loudspeaker signals $y_v$[n]+$m_v$[n] and the microphone signals $dm_w$[n]=$e_w$[n]+$m_w$'[n] and calculates a quality function value and sets the measurement signal gain dependent thereon. However, other examples for calculating the quality function QLTY in the multi-channel case are discussed below with respect to FIG. 8.

Figure 8:
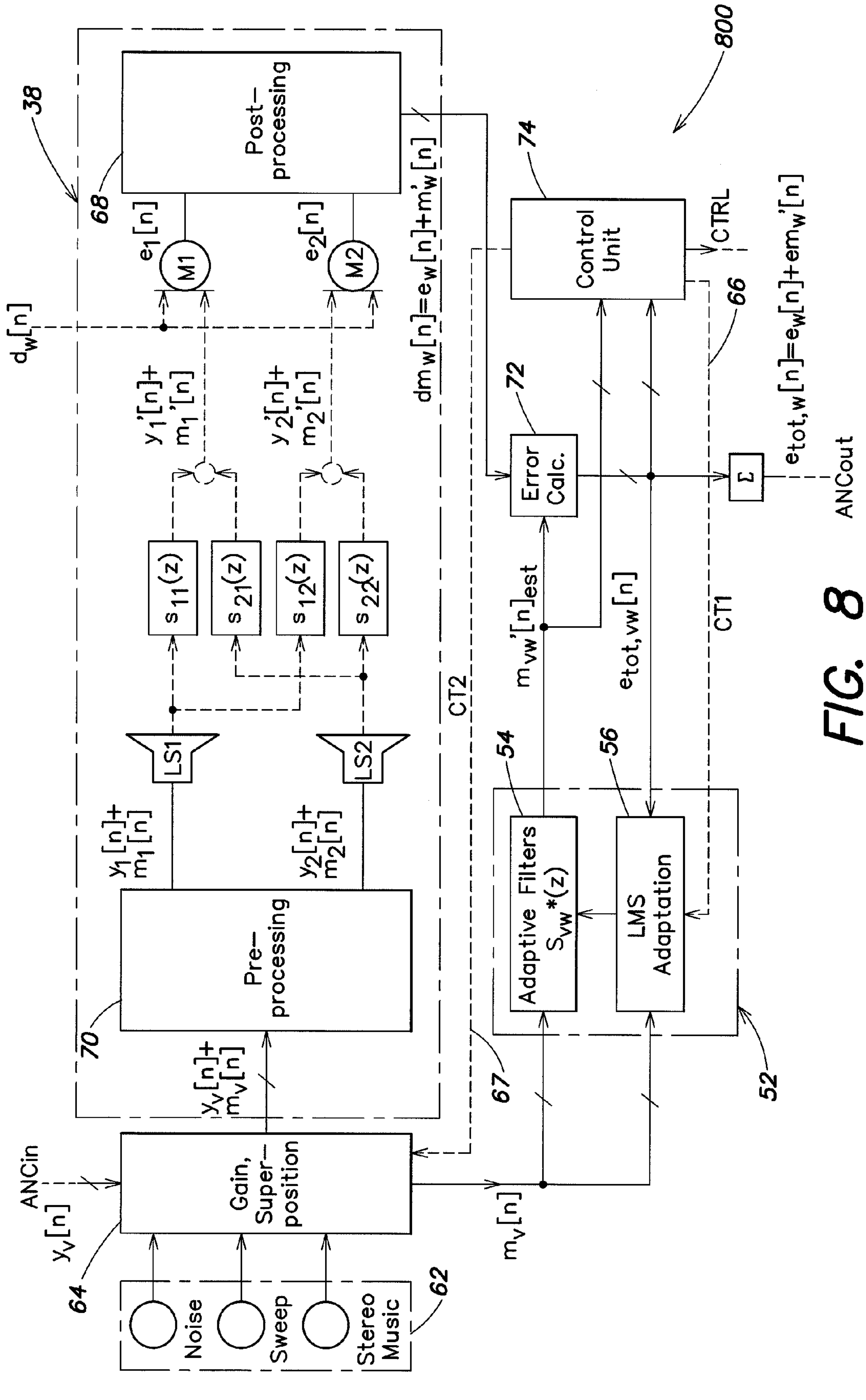
FIG. 8 illustrates a multi-channel ANC system that includes a secondary path identification system.

FIG. 8 illustrates a multi-channel ANC system 800 which has a similar configuration to the ANC system in FIG. 7A. The system 800 is only shown with a secondary path 38 having a transfer matrix $S_{vw}(z)$ and select other components for system identification to simplify the following description. In this embodiment, the multi-channel ANC system 800 includes two loudspeakers and two microphones. The measurement signal m[n] used for system identification and estimation of the secondary path transfer function S*(z) is generated by one of the measurement signal sources 62. The measurement signal m[n] may include a noise signal, a linear or logarithmic frequency sweep signal or a music signal. However, any measurement signal m[n] should be uncorrelated with the reference signal x[n] and thus with the residual error signal e[n] of the ANC system.

A first processing unit 64 is connected to the measurement signal sources 62. The processing unit 64 selects one of the signal sources 62, and provides a measurement signal that is a superposition of a different signal provided by the selected signal source 62. The first processing unit 64 also provides a frequency dependent gain shaping capability. That is, a frequency dependent gain may be imposed on the measurement signal m[n], wherein the frequency dependent gain depends on a control signal CT2 on line 67. Furthermore, the first processing unit 64 may be configured to distribute the measurement signal m[n] to each of the loudspeakers LS1 and LS2. In the present example, the first processing unit 64 provides a 2-dimensional vector $m_v$[n] that includes the measurement signals $m_1$[n] and $m_2$[n], which are supplied to the loudspeakers LS1 and LS2, respectively. The filtered reference signals $y_v$[n] is also provided to the loudspeakers such that the superposition $m_v$[n]+$y_v$[n] is radiated by the corresponding loudspeakers.

The acoustic signals arriving at the microphones Mw are the superpositions $m_w$'[n]+$y_w$'[n], where $m_w$'[n] is the vector of modified measurement signals and $y_w$'[n] is the vector of compensation signals for suppressing the corresponding disturbing noise signals $d_w$[n] at the respective listening positions where noise cancelling is desired. The z-transform $m_w$'(z) of the modified measurement signal vector $m_w$'[n] may be calculated as follows:

$$m'_w(z) = \sum_{v=1}^{V} S_{vw}(z) m_v(z) \text{ for } w = 1, \ldots, W,$$

where $m_v(z)$ is the vector of z-transforms for the corresponding measurement signals $m_v$[n]. The compensation signals $y_w$'[n] may be calculated in a similar manner.

The microphones M1, M2 provide ANC error signals $e_1$[n] and $e_2$[n] to the post processing unit 68, respectively, which may generally be denoted as W-dimensional error vector $e_w$[n]=$y_w$'[n]+$d_w$[n]. The error vector is superposed with the modified measurement signal $m_w'[n]$. A pre-processing unit 70 and a post-processing unit 68 include the analog-to-digital and the digital-to-analog converters, a sample rate conversion (upsampling and downsampling) unit, and filters, which will be described below in further detail (see FIG. 9).

The modified measurement signals $m_w'[n]$, which are superposed to the error signals $e_w[n]$, can disturb the active noise control system (i.e., the adaptive filter, the LMS adaptation unit). Thus, the active noise control system is removed from the microphone output signals via the estimated secondary path system $S_{vw}^*(z)$ (see. FIG. 8: system 54). The ANC error signal $e_w[n]$ is uncorrelated noise and, thus, does not introduce any systematic errors in the secondary path estimation system; however, it can introduce statistic errors. Therefore, the superposition $dm_w[n]=e_w[n]+m_w'[n]$ may be used as a desired "target signal" for system estimation, i.e., the adaptive filter 54 should be adapted such that on average its output matches the desired target signal. In this embodiment, the transfer function of the adaptive filter $S_{vw}^*(z)$ represents the real transfer characteristic of the secondary path system 38.

The adaptive filter 54 may "simulate" the modified measurement signal vector $m_w'[n]_{est}$. The simulated (i.e., estimated) signal vector $m_w'[n]_{est}$ may then be subtracted from the microphone signals, such that the residual error signal equals $e_{tot,w}[n]=e_w[n]+(m_w'[n]-m_w'[n]_{est})=e_w[n]+em_w'[n]$ (which approximately equals $e_w[n]$ if the quality of the secondary path estimation is sufficiently high; i.e., if $S_{vw}^*(z)\approx S(z)$, then $e_w[n]+(m_w'[n]-m_w'[n]_{est})\approx e_w[n]$). However, the error $em_w[n]$ due to the system estimation is uncorrelated noise for the active noise control and thus does not introduce any systematic errors. Consequently the total error signal $e_{tot,w}[n]$ may be used for the active noise control.

The estimated transfer function $S_{vw}^*(z)$ may be a matrix, wherein each component of the matrix represents the transfer characteristics from one of the V loudspeakers to one of the W microphones. Consequently W×V components of the modified measurement signal can be calculated which are denoted as $m_{vw}'[n]$. The superposition:

$$m'_w(z)_{est} = \sum_{v=1}^{V} m'_{vw}(z)_{est} \text{ where } m'_{vw}(z)_{est} = S^*_{vw} \times m_v(z)$$

provides the total simulated modified measurement signal at each microphone with index w.

Where the transfer matrix $S_{vw}^*(z)$ is adapted component by component, the corresponding W×V components of the error signal are calculated. However, only W microphone signals are available where each microphone signal $dm_w[n]$ includes a superposition from V measurement signals radiated from the V loudspeakers. Regarding the $i^{th}$ component of the transfer matrix $S_{iw}^*(z)$, the corresponding desired target signal $dm_{iw}[n]$ is calculated from the microphone signal $dm_w[n]$ by subtracting therefrom all other simulated components except the $i^{th}$. That is:

$$dm_{iw}[n] = dm_w[n] - \sum_{\text{each } v \neq i} m'_{vw}[n]_{est}.$$

The corresponding total is therefore calculated as:

$$e_{tot,iw}[n]=dm_{iw}[n]-m_{iw}'[n]_{est}.$$

The transfer function $S_{iw}^*(z)$ and the subsequent transfer function $S_{i+1,w}^*(z)$ are adapted based on the above referenced error signal $e_{tot,iw}[n]$. This error calculation is performed by the error calculation unit 72.

The LMS adaptation unit 56 calculates the filter coefficients of the adaptive filters $S_{vw}^*(z)$ using the LMS algorithm, and provides an optimal estimation of the matrix of secondary path transfer functions $S_{vw}^*(z)$. The error signal $e_{tot,vw}[n]$ may be separated into the component $em_{vw}'[n]$, which is correlated with the measurement signal $m_v[n]$, and the component $e_w[n]$, which is correlated with the compensation signal $y_w'[n]$ and the noise signal $d_w[n]$. Although these components cannot be easily separated, this does not necessarily adversely affect the secondary path estimation or the active noise control. Since the output signals $y_w'[n]$ and $m_w'[n]$ of both parts of the system (active noise control with the adaptive filter 34 and secondary path system identification with the adaptive filter 54) and the respective error signal components $e_{vw}[n]$ and $em_{vw}'[n]$ are uncorrelated, (i) the error signal component $e_{vw}[n]$ is uncorrelated noise for the secondary path system identification, and (ii) the error signal component $em_{vw}'[n]$ is uncorrelated noise for the active noise control. As explained above, uncorrelated noise does not have a negative impact on system identification where its respective SNR (signal-to-noise ratio) is above a defined threshold value.

The error signal $e_{tot,vw}[n]$ may be summed over the V components since the V loudspeakers provide a vector signal as follows:

$$e_{tot,w}[n] = \sum_{v=1}^{V} e_{tot,vw}[n] = e_w[n] + em'_w[n].$$

A control unit 74 receives the estimated modified measurement signal $m_{vw}'[n]_{est}$ and the error signal $e_{tot,vw}[n]$. The control unit 74 is configured to monitor and assess the quality of the secondary path estimation and, dependent on the quality assessment to provide control signals CT1, CT2 for the LMS adaptation unit 56 and the first processing unit 64 via lines 66 and 67. The signal-to-noise ratio may, for example, be used as a quality measure for system estimation as explained above with respect to FIG. 7B. The above mentioned quality function may also be calculated using the total error signal $e_{tot,vw}[n]$ and the desired target signal $dm_{vw}[n]$. In this example, for every one of the V×W components of the estimated secondary path transfer function $S_{vw}^*(z)$, a corresponding quality function $QLTY_{vw}$ may be determined. Furthermore, the quality function may be a function of frequency such that the quality of the system estimation may be separately assessed in different spectral ranges or at different frequencies. For example, the quality function may be calculated using the following FFT (fast Fourier transform) algorithm:

$$QLTY_{vw}[k]=FFT\{e_{tot,vw}[n]\}/FFT\{dm_{vw}[n]\},$$

where the symbol n is a time index, and the symbol k is a frequency index.

As set forth above with respect to the single-channel ANC system in FIG. 7, the quality function may be compared to a threshold to determine whether the estimation has an acceptable quality. Of course, the threshold may be frequency dependent and different for the considered components of the sought transfer matrix function.

When the secondary path system has an unacceptable quality for a period of time, the gain of the measurement signal $m_v[n]$ may be increased, wherein the gain varies over frequency, since the quality function varies over frequency. Subsequently, system identification is repeated with the adjusted measurement signal $m_v[n]$. If the secondary path system has an acceptable (good) quality, the transfer function $S_{vw}^*(z)$ for the estimated secondary path system (or the respective impulse responses) may be stored for further use in active noise control. In addition, the frequency dependent gain of the measurement signal $m_v[n]$ may be reduced and/or system identification may be paused, as long as the quality remains high. The measurement signal gain of the measurement signal $m_v[n]$ is set by the control unit 74 by outputting a quality function dependent control signal CT2 to the first processing unit 64. Further, the adaptation unit 56 controlling the adaptation of the adaptive filter 54 may be controlled via control signal CT1, also output from the control unit 74. As already mentioned, the adaptation may be paused if good quality has been reached. An additional control signal CTRL output from the control unit 74 may control other components of the active noise control system such as, for example, the adaptation unit 36 (see FIG. 7A). In some cases, it may be useful to pause the overall active noise control system, except the part performing the secondary path system identification where the actual estimated secondary path transfer function has an unacceptable (or bad) quality, e.g., the quality function is below the predefined threshold.

The overall active noise system that includes the secondary path system identification (whether single channel or multi channel) has at least three modes of operation. During a first mode, the active noise control may be paused or switched off when the secondary path system identification is active. This mode is useful when the actual secondary path transfer function being estimated has an unacceptable quality. During such a condition, the ANC system may operate incorrectly and even increase the noise level instead of suppressing it. Thus, the active noise control is paused until the estimated secondary path transfer function has an acceptable quality (e.g., where the quality exceeds a given threshold).

In a second mode, the secondary path system identification and the active noise cancelling are active. In this mode, the measurement signal $m_v[n]$ influences the noise cancelling and the anti-noise (i.e., the compensation signal $y_w'[n]$) generated by the ANC system influences the secondary path identification. As explained above, this interaction is not problematic since the relevant signals in the two parts of the system are uncorrelated. That is, the compensation signal $y_w'[n]$ of the ANC system and the measurement signal received by the microphones $m_w'[n]$ are uncorrelated. Therefore, the respective filter units 54, 34 are "properly" adapted as long as the signal-to-noise ratio remains above a defined limit.

In a third mode, where the available estimated secondary path transfer function has an acceptable quality (i.e., where the quality function exceeds the given threshold), the secondary path system identification is paused in order to prevent the measurement signal $m_v[n]$ from adversely influencing the active noise control.

During the aforesaid modes of operation, when the secondary path system identification is active, the step size of the adaptation process (see adaptation unit 56) may be adjusted dependent on the actual value of the quality function QLTY.

A system distance may also be used as quality function QLTY or $QLTY_{vw}$, respectively. The system distance may be used to assess "how far away" the approximation of the estimated secondary path system is from the real system; i.e., the difference of the approximation and the real system. Thus, the system distance is measured as follows:

$$DIS_{vw}=1-S_{vw}^*(z)/S_{vw}(z).$$

An ideal estimation (i.e., $S_{vw}^*(z)=S_{vw}(z)$) provides a system distance of zero. The higher the absolute value of the system distance, the lower the quality of the estimation. From the following equation, it is shown that the quality function also represents the system distance:

$$QLTY_{vw}[k]=FFT\{e_{tot,vw}[n]\}/FFT\{dm_{vw}[n]\}.$$

Figure 9A:
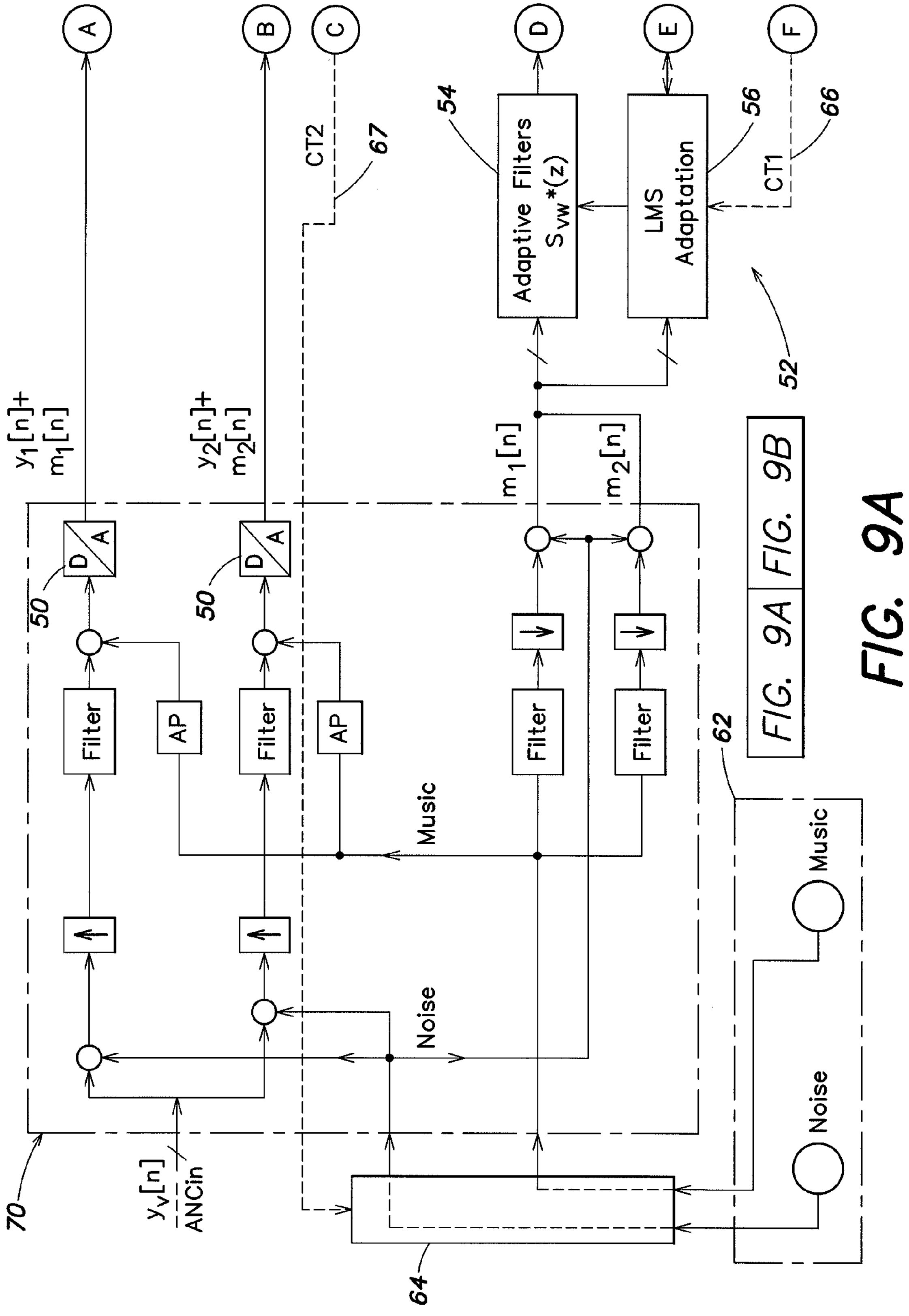
FIG. 9 illustrates, in greater detail, the multi-channel ANC system in FIG. 8.
Figure 9B:
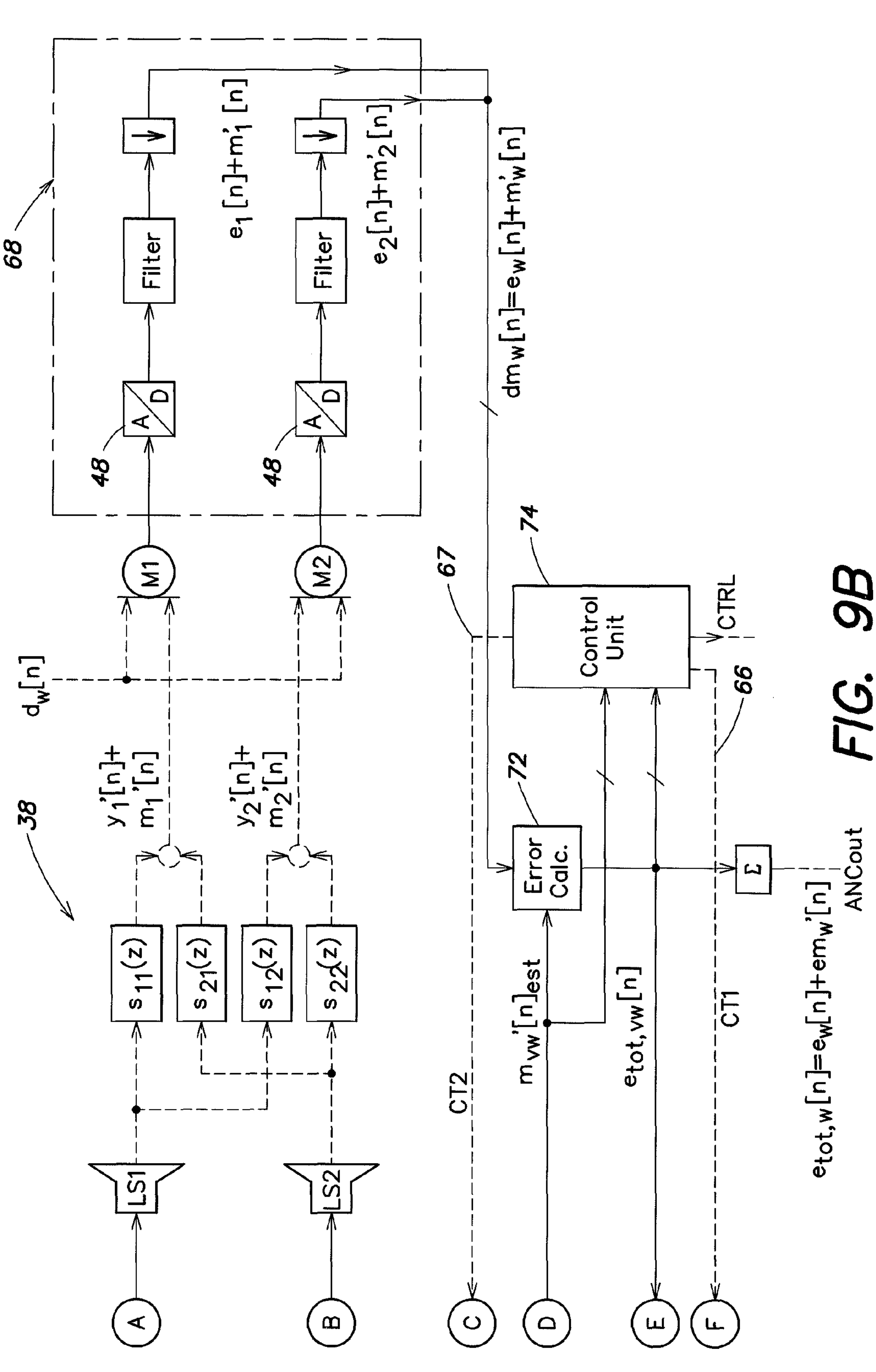

Referring to FIG. 9, the pre-processing and post-processing units 70 and 68 are illustrated in more detail. Since the audio frontend (e.g., the audio A/D-converters and D/A-converters), for example, may operate at sampling frequencies of $f_S$=44.1 kHz or $f_S$=48 kHz whereas the ANC system may operate at sampling frequencies of $f_S/32$, i.e. ≈1375 Hz or 1500 Hz, respectively, the pre- and post-processing units 70, 68 include sample rate converters (interpolators and decimators) and corresponding interpolation and decimation filters. When noise is used as measurement signal m[n], it is upsampled to the sampling frequency $f_S$ of the audio frontend before being supplied to the secondary path. Furthermore, the microphone signals may be digitized with a sampling frequency $f_S$ and then down-sampled to the clock frequency of the ANC system. The pre-processing unit 70 may also provide a (optionally weighted) superposition of noise and music as a measurement signal $m_v[n]$. As illustrated in FIG. 9, the music signal is, on the one hand, transmitted via the D/A-converters 50 of the pre-processing unit 70, the "real" secondary path system 38, and the post-processing unit 68 to the error calculation unit 72. On the other hand, the music signal is transmitted via the filter and the downsampling unit of the pre-processing unit 70, the "simulated" secondary path system (i.e. adaptive filter 54) to the error calculation unit 72. At the error calculation unit 72, the music signal is (approximately) eliminated from the microphone signals $dm_w[n]=e_w[n]+m_w'[n]$ by subsequently subtracting the simulated secondary path outputs due to the music signal $m_{vw}'[n]_{est}$ from the microphone signal. For this purpose the music signal transmitted via the "real" secondary path system 38 and the signal transmitted via the "simulated" secondary path system 52 have the same phase when arriving at error calculation unit 72. However, since the signal path that includes the real secondary path system 38 and the signal path that includes the simulated secondary path system 52 include different signal processing components (upsampling unit, downsampling unit, filters, A/D-converter and D/A-converters, etc.), the all-passes filters may be included in the pre-processing unit 70 in order to provide the same signal phase shift in both signal paths, the one including the real secondary path 38 and the one including the simulated secondary path 52.

While various embodiments of the present invention have been disclosed, it will be apparent to those of ordinary skill in the art that many more embodiments and implementations are possible within the scope of the invention. Accordingly, the present invention is not to be restricted except in light of the attached claims and their equivalents.

What is claimed is:

1. An active noise cancellation system for reducing, at a listening position, power of a noise signal radiated from a noise source to the listening position, the system comprising:

an adaptive filter that receives a reference signal representing the noise signal, and provides a compensation signal in response to the received reference signal;

a signal source that provides a measurement signal;

an acoustic actuator that radiates the compensation signal and the measurement signal to the listening position;

a microphone that receives a first signal that is a superposition of the radiated compensation signal, the radiated measurement signal, and the noise signal at the listening position, and provides a microphone signal in response to the received first signal;

a secondary path comprising a secondary path system that represents a signal transmission path between an output of the adaptive filter and an output of the microphone;

an estimation device that estimates a transfer characteristic of the secondary path system in response to the measurement signal and the microphone signal;

a second microphone, where the first and second microphones are located in different listening positions where the power of the noise signal is to be reduced, the microphones providing a vector of microphone signals; and a second acoustic actuator, where the first and second acoustic actuators radiate a vector of compensation signals provided by the adaptive filter, and radiate a vector of measurement signals provided by the signal source.

2. The system of claim 1, where the estimation device attenuates at least one measurement signal component in the microphone signal to provide an error signal.

3. The system of claim 2, where the estimation device comprises a second adaptive filter that is responsive to the measurement signal and the error signal, and provides an estimation of the measurement signal as received by the microphone.

4. The system of claim 3, where the estimation device subtracts the estimation of the measurement signal from the microphone signal to at least partially suppress the one or more measurement signal components in the microphone signal.

5. The system of claim 3, further comprising a control device that monitors and assesses quality of the estimation of the secondary path system.

6. The system of claim 5, where the control device provides a control signal for controlling frequency dependent gain of a pre-processing device, the control signal depending on the quality of the estimation.

7. The system of claim 1, where the estimation device attenuates one or more measurement signal components in the vector of microphone signals.

8. The system of claim 7, where the estimation device comprises a multi-input/multi- output adaptive filter that is responsive to the vector of measurement signals and the vector of error signals, and provides an estimation of the measurement signals as received by the microphones, where the estimation comprises a matrix of estimated measurement signals, where each matrix component represents the estimated measurement signal of a corresponding pair of a respective one of the acoustic actuators and a respective one of the microphones.

9. The system of claim 8, where the estimation device subtracts the matrix components of the estimated measurement signals from corresponding components of the vector of microphone signals to provide a matrix of error signals, each component of which corresponds to a pair of a respective one of the acoustic actuators and a respective one of the microphones.

10. The system of claim 1, further comprising:

a first processing device that superposes the measurement signal and the compensation signal, and supplies at least one resulting sum signal to the at least one acoustic actuator.

11. The system of claim 10, further comprising a second signal source that provides a second measurement signal, where the first processing device superposes the measurement signal, the second measurement signal and the compensation signal, and supplies one or more resulting sum signals to the at least one acoustic actuator.

12. The system of claim 11, where the first processing device comprises an all-pass filter that compensates for phase differences between different measurement signals.

13. The system of claim 10, where the measurement signal is sampled at a sample rate, and the first processing device comprises a sample rate converter that adjusts the sampling rate of the measurement signal to match a sample rate of an audio system driving the at least one acoustic actuator.

14. The system of claim 10, where the measurement signal is sampled at a sample rate, and the first processing device comprises a sample rate converter that adjusts the sampling rate of the measurement signal to match a sample rate of the estimation device for estimating the transfer characteristic of the secondary path system.

15. An active noise cancellation system for reducing, at a listening position, power of a noise signal radiated from a noise source to the listening position, the system comprising:

an adaptive filter that receives a reference signal representing the noise signal, and provides a compensation signal in response to the received reference signal;

a signal source that provides a measurement signal;

an acoustic actuator that radiates the compensation signal and the measurement signal to the listening position;

a microphone that receives a first signal that is a superposition of the radiated compensation signal, the radiated measurement signal, and the noise signal at the listening position, and provides a microphone signal in response to the received first signal;

a secondary path comprising a secondary path system that represents a signal transmission path between an output of the adaptive filter and an output of the microphone;

an estimation device that estimates a transfer characteristic of the secondary path system in response to the measurement signal and the microphone signal; and a pre-processing device connected upstream of the at least one acoustic actuator and downstream of the adaptive filter, the pre-processing device comprising a device for imposing a frequency dependent gain on the measurement signal.

16. A method for reducing, at a listening position, power of a noise signal radiated from a noise source to the listening position, the method comprising:

adaptively filtering a reference signal representing the noise signal via an adaptive filter to provide a compensation signal at a first sample rate;

providing a measurement signal;

an acoustic actuator;

receiving a first signal via at least one microphone, where the first signal is a superposition of the radiated compensation signal, the radiated measurement signal, and the noise signal at the listening position; and estimating a transfer characteristic of a secondary path system responsive to the measurement signal and the first signal;

where the secondary path system represents a signal transmission path between an output of the adaptive filter and an output of the at least one microphone;

adjusting the first sampling rate to match a second sample rate of an audio system driving the acoustic actuator;

all-pass filtering the measurement signal to provide substantially the same signal phase shift in both signal paths, the signal path providing the measurement signal and the compensation signal; and superposing the measurement signal and the compensation signal and providing a sum signal indicative thereof to the acoustic actuator.

17. The method of claim 16, where the step of estimating the transfer characteristic comprises:

at least partially suppressing in the first signal one or more measurement signal components to provide an error signal.

18. The method of claim 16, where the step of estimating the transfer characteristic comprises:

adaptively filtering the measurement signal to provide an estimation of the measurement signal as received by the at least one microphone.

19. The method of claim 18, where the step of estimating the transfer characteristic further comprises:

subtracting the estimation of the measurement signal from the first signal to at least partially suppress one or more measurement signal components in the first signal to provide an error signal.

20. An active noise cancellation system for reducing, at a listening position, power of a noise signal radiated from a noise source to the listening position, the system comprising:

an adaptive filter that receives a reference signal representing the noise signal, and provides a compensation signal at a first sample rate;

a signal source that provides a measurement signal;

an acoustic actuator that radiates the compensation signal and the measurement signal to the listening position;

a microphone that receives a first signal that is a superposition of the radiated compensation signal, the radiated measurement signal, and the noise signal at the listening position, and provides a microphone signal;

a secondary path comprising a secondary path system that represents a signal transmission path between an output of the adaptive filter and an output of the microphone;

an estimation device that estimates a transfer characteristic of the secondary path system in response to the measurement signal and the microphone signal; and a pre-processing device configured to superpose the measurement signal and the compensation signal and provide resulting sum signals to the acoustic actuator, where the pre-processing device comprises a sample rate converter that adjusts the first sampling rate to substantially match a second sampling rate of an audio system driving the acoustic actuator, where the pre-processing device comprises an all-pass filter that provides substantially the same phase shift in a first signal path that provides the measurement signal and in a second signal path that provides the compensation signal.

* * * * *